United States Patent [19]

Collier et al.

[11] Patent Number: 5,234,559
[45] Date of Patent: Aug. 10, 1993

[54] APPARATUS FOR DIRECT BLOTTING AND AUTOMATED ELECTROPHORESIS, TRANSFER AND DETECTION AND PROCESSES UTILIZING THE APPARATUS THEREOF

[75] Inventors: Charles F. Collier, Wilmington, Del.; David J. Regester, West Grove, Pa.; Charles W. Robertson, Rockland, Del.

[73] Assignee: E. I. Du Pont de Nemours and Company, Wilmington, Del.

[21] Appl. No.: 945,553

[22] Filed: Sep. 16, 1992

Related U.S. Application Data

[63] Continuation of Ser. No. 816,513, Dec. 31, 1991.

[51] Int. Cl.$^5$ .................. G01N 27/26; G01N 27/447
[52] U.S. Cl. ........................... 204/182.8; 204/299 R
[58] Field of Search ........................ 204/299 R, 182.8

[56] References Cited

U.S. PATENT DOCUMENTS

| | | | |
|---|---|---|---|
| Re. 30,595 | 4/1981 | Covington et al. | 422/63 |
| 3,047,489 | 7/1962 | Raymond | 204/299 |
| 3,062,731 | 11/1962 | Durrum | 204/180 |
| 3,129,158 | 4/1964 | Raymond et al. | 204/180 |
| 3,674,678 | 7/1972 | Post, Jr. | 204/299 |
| 3,705,845 | 12/1972 | Everaerts | 204/180 R |
| 3,948,753 | 4/1976 | Arlinger | 204/299 |
| 4,152,390 | 5/1979 | Nosco et al. | 422/63 |
| 4,589,965 | 5/1986 | Kreisher | 204/182.8 |
| 4,622,124 | 11/1986 | Kreisher | 204/301 |
| 4,631,120 | 12/1986 | Pohl | 204/182.8 |
| 4,631,422 | 12/1986 | Piasecki | 307/300 |
| 4,726,889 | 2/1988 | Love et al. | 204/182.8 |
| 4,812,216 | 3/1989 | Hurd | 204/182.8 |
| 4,818,360 | 4/1989 | Hurd | 204/299 |
| 4,889,606 | 12/1989 | Dyson et al. | 204/299 R X |
| 4,913,791 | 4/1990 | Hurd et al. | 204/299 R |
| 4,994,166 | 2/1991 | Fernwood et al. | 204/299 R |
| 5,013,420 | 5/1991 | Schuette | 204/299 R |
| 5,102,524 | 4/1992 | Dutertie | 204/299 R |

FOREIGN PATENT DOCUMENTS

| | | | |
|---|---|---|---|
| 1-112147 | 4/1989 | Japan | 204/299 R |
| 8702132 | 4/1987 | PCT Int'l Appl. | 204/299 R |
| 2147609 | 5/1985 | United Kingdom | 204/299 R |

OTHER PUBLICATIONS

Beck and Phol, EMRO J, 3(12), 2905, 1984.
Hoefer Scientific Instruments Electrophoresis Instruments and Accessories 1990-1991.

Primary Examiner—John Niebling
Assistant Examiner—John S. Starsiak, Jr.

[57] ABSTRACT

A separation and direct blot transfer module useful in gel electrophoresis is disclosed in which a transfer membrane stabilized by a frame is moved substantially orthogonally relative to the plane of the separation gel while in minimal contact with the end of the gel toward which molecular fragments are driven electrophoretically. The frame moves at a controlled velocity in a selected direction away from a line of contact that generates a controlled tension in the membrane which is a function of the loading on the line of contact. The module is particularly amenable to automated processing. Apparatus for automated separation, transfer, membrane processing, detection and identification is disclosed in which the module of the invention is employed.

16 Claims, 10 Drawing Sheets

APPARATUS FOR DIRECT BLOTTING AND AUTOMATED ELECTROPHORESIS, TRANSFER AND DETECTION AND PROCESSES UTILIZING THE APPARATUS THEREOF

This is a continuation of application Ser. No. 07/816,513, filed Dec. 31, 1991, pending.

FIELD OF THE INVENTION

This invention relates to the field of gel electrophoresis. More particularly, this invention relates to apparatus for effecting electrophoresis across a gel and to a transfer membrane, so that the electrophoretically driven molecular components are accurately separated on the membrane, and processes using the apparatus herein.

BACKGROUND OF THE INVENTION

Gel electophoresis is an important tool in analytical and clinical laboratories. It takes advantage of the electrokinetic differences of ions in an electric field to accomplish separation of complex mixtures so that the components can be identified or isolated. A gel, such as agarose or polyacrylamide, is cast in a mold to produce, most commonly, an extended block of rectangular cross-section which is relatively thin. Wells are formed at one end. The block is supported and immersed in a buffer solution in apparatus having an electrode at each end. The wells are loaded with a solution containing the material under study, such as nucleic acids, and the gel is subjected to an electric field providing a high gradient along the length. The molecules migrate toward the distant electrode at different rates dependent on their mobility, which is a function of size and charge density. There are many variations of this methodology: the gels may have density gradients, either continuous or in steps; the voltage or temperature may be controlled or varied, as by controlled polarity reversal for example; and gradients may be established in pH or in concentration.

Regardless of the particular scheme employed, two basic modes of operation are used. In the usual mode, the separation is run for a finite time and then the separated molecules are read in place by some known technique which renders the pattern readable such as staining or marking with a radioactive or fluorescent material. Alternatively, the pattern is transferred in the orthogonal direction by one of various known techniques such as Southern blotting, pressure blotting, vacuum blotting, or electroblotting (transverse electric field) or the like. The separated molecules are immobilized on blotting paper or more usually, a membrane of nylon or the like where they can be identified by any of such procedures as selective dyeing, radioactive marking, fluorescence, and chemiluminescence. The procedure may employ a suitable probe to attach the marking means to the separated species.

In the other mode, often used in preparatory electrophoresis, the gel separation is run continuously (or for an extended time) and the separated species are allowed to migrate off the end of the gel into a stationary collection chamber. From time to time in a controlled manner this chamber is emptied to yield a stepwise separation of the components of the starting mixture.

In U.S. Pat. Nos. 4,631,120 and 4,631,422, Pohl teaches apparatus and method for a variant of the latter process, called direct blotting. Pohl provides one or more collecting surfaces mounted on a conveyer belt or tape and advances the belt so that it slides over the end of the gel to collect separated elemental particles and transport them with the belt away from the gel to a location where further processing such as identification may be performed. Both vertical and horizontal embodiments are disclosed. In an article by Beck and Pohl, (EMRO J, 3(12), 2905, 1984) the authors emphasize that in such a system intimate contact of the belt with the end of the gel is obtained by guiding "axles" (i.e., rollers) for the belt. The method and apparatus is described as especially amenable to automation.

A disadvantage of the apparatus of Pohl is the lack of planar stability and tension control of the collecting surface which is inherent in use of a tape or belt supported only at relatively remote lines of contact by rollers. Contact pressure is poorly controlled. Additionally contact of a roller on the collecting surface is possibly deleterious by both damage to the surface and by possible removal of some of the separated species and subsequent reprinting of the material removed onto the surface at an incorrect location.

Further, the apparatus of Pohl is not adapted to the handling and identification of a multiplicity of samples in sequence especially when the separated elements are transferred to membranes and these must be transported through a number of subsequent and different processing steps to carry out identification or the like.

U.S. Pat. No. 3,948,753 to Arlinger discloses apparatus for isotachophoretical separation, consisting of a capillary tube communicating with the sampling zone of a sampling column between electrolytes of different electrical potentials.

U.S. Pat. No. 3,705,845 to Everaerts discloses a method in counterflow isotachophoresis. A column with two electrodes holds a sample comprising ions of different mobility and to be separated. First and second electrolytes having higher and lower, respectively, mobility than the sample ions are introduced. After voltage and pressure are applied, a boundary between ion zones is detected and a control signal generated.

U.S. Pat. No. 3,047,489 to Raymond is directed to apparatus for zone electrophoresis. It discloses a preferred array of buffer medium chambers, associated electrodes, cooling plates and various buffers and wicks. U.S. Pat. No. 3,129,158 to Raymond et al., disclose a process for gel electrophoresis, including means to prepare the gel in preferred dimension, shape and position for conducting electrical current through the gel and for applying specimen mixture thereto.

U.S. Pat. No. 3,062,731 to Durrum discloses an agar-agar system, and additive suitable for electrophoretic analysis.

U.S. Pat. No. 4,622,124 is directed to a device for horizontal electroblotting of electrophoretically transferred material. A liquid tight container is provided having a support assembly horizontally disposed in a chamber defined by the container. Electrodes are located below and above the support assembly, and a bubble diverting barrier is provided to prevent uneven blotting.

U.S. Pat. No. 4,589,965 discloses a method for electroblotting whereby an electrophoretically resolved material in a gelatin sheet is transferred to a membrane with high pattern definition and resolution. The gelatin sheet is contacted with an immobilizing material, with the combination sandwiched between two plate electrodes. An electric current is applied to the electrodes of the assembly.

U.S. Pat. No. 3,674,678 discloses an apparatus for conducting electrophoretic analysis comprising a container filled with a conductive gel, two electrodes in the container, and means for effecting voltage across the gel. The container includes deep reservoirs at opposing ends and mid-section wells to accommodate samples.

It is an object of the present invention to provide electrophoretic apparatus that positions a transfer membrane relative to electrophoretic gel so that the electrophoretic transfer to the membrane is conducted in a controlled fashion. It is a further object of the present invention to provide this transfer so that the electrophoretic pattern upon visualization is remarkably clear and reproducible. A feature of the present invention is the means to provide a controlled tension on the transfer membrane as it contacts the electrophoretic gel. It is an advantage of the present invention that the apparatus disclosed herein is amenable to an automated process including a variety of processing stations. These and other objects, features and advantages of the invention will become apparent upon having reference to the following description.

SUMMARY OF THE INVENTION

There is disclosed herein apparatus for gel electrophoresis in which molecular fragments in a solution are separated electrophoretically across a gel, comprising:

(a) an electrophoresis module comprising the gel including the solution with molecular fragments, and means for effecting electrophoresis therealong;

(b) an electrophoretic transfer membrane comprising a rigid frame that supports a flexible membrane along portions of the periphery thereof;

(c) means for moving the electrophoretic transfer membrane relative to and in contact with the electrophoresis module, so that the molecular fragments are received on the flexible membrane from gel; and (d) means for tensioning the flexible membrane as the flexible membrane moves in proximity to the electrophoresis module.

In the electrophoresis module (a) the means for effecting electrophoresis comprises (i) a cassette having a first reservoir adapted to receive buffer solution and a first electrode and an extended portion adapted to receive the gel, with the first reservoir positioned at a first location relative to the extended portion. It also includes (ii) a second reservoir having buffer solution and a second electrode and positioned at a second location relative to the extended portion. The gel including solution with molecular fragments is positioned within the extended portion and between the first and second reservoirs, and a voltage differential is applied between the first and second electrodes to electrophoretically translate and separate the molecular fragments toward one end of the gel proximate to the electrophoretic transfer membrane (b).

There is also disclosed herein a process for gel electrophoresis of molecular fragments, comprising:

(a) introducing a gel including a solution with the molecular fragments therein, into an electrophoresis module having means for effecting electrophoresis therealong;

(b) positioning an electrophoretic transfer membrane for contact with the gel, the electrophoretic transfer membrane comprising a rigid frame that supports a flexible membrane along portions of the periphery thereof;

(c) moving the electrophoretic transfer membrane relative to and in proximity to the electrophoresis module, so that the molecular fragments are received on the flexible membrane from the gel; and (d) tensioning the flexible membrane as the electrophoretic transfer membrane moves in proximity to the electrophoresis module.

DETAILED DESCRIPTION OF THE INVENTION

Figure 1:
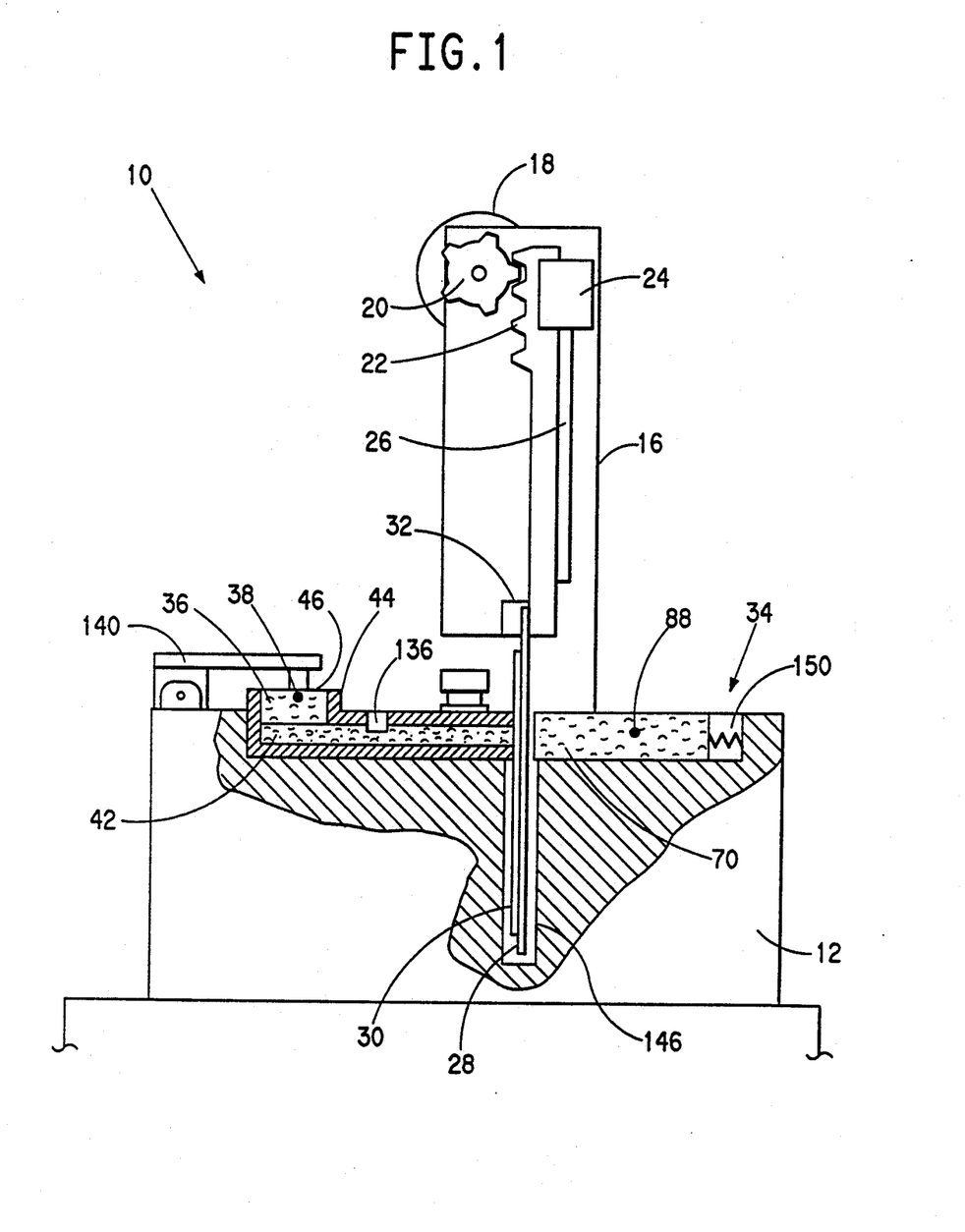
FIG. 1 is an elevational view in partial cross-section of according to the invention.
Figure 2:
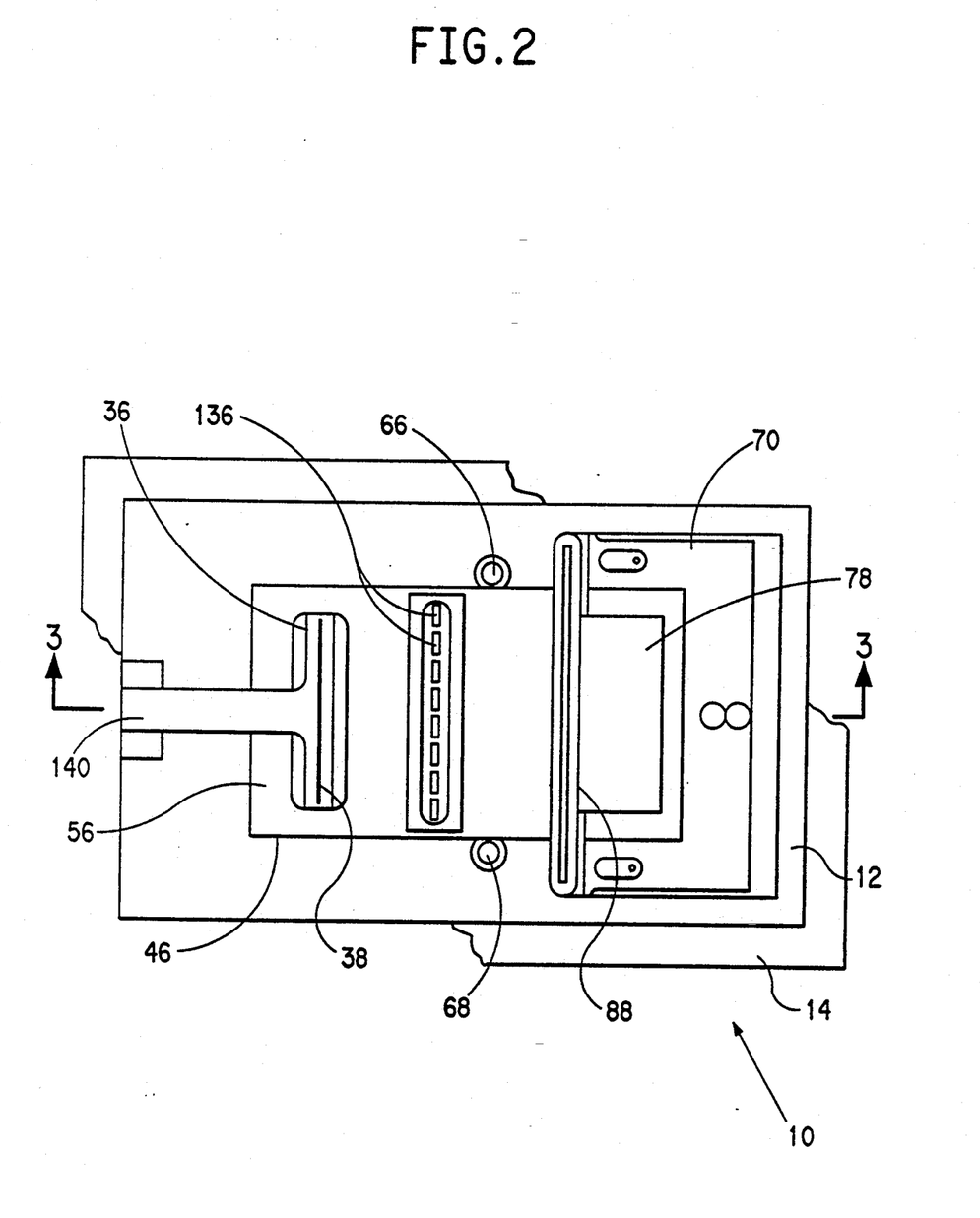
FIG. 2 is a plan view of the apparatus of the invention.

Apparatus of the invention as seen in FIGS. 1 and 2 is generally indicated by 10 Base 12 stands on leveling table 14. We prefer to use a leveling table such as Catalogue Number 170-4046 sold by Bio-Rad. Fastened to base 12 by fasteners not shown in the figure is support frame 16 which holds stepping motor 18 also fastened thereto by means not shown. Pinion 20 is mounted on the shaft of motor 18 and meshes with rack 22 which is constrained to vertical sliding motion by guide 24 which is fastened to support frame 16 and also serves to properly maintain the gear mesh. This apparatus is collectively a motor and drive train assembly and is utilized to move the electrophoretic transfer membrane relative to the electrophoresis module. Rack 22 is part of membrane carrier 26. An electrophoretic transfer membrane, best seen in FIG. 5, includes a frame 28 which supports membrane 30 and which is clamped along its upper edge to carrier 26 by clamp 32 which is fastened by means not shown.

Horizontal electrophoresis module 34 stands atop base 12 nested into cavity 150. The module 34 comprises a gel cassette 44, for casting and holding gel 42 and a slideable assembly 70. Cassette 44 has a first reservoir 36 at one end having a transverse wire electrode 38 which is mounted on pivoted arm 140. A preferred material of construction for the electrode is platinized titanium wire held in a nonconductor molded so that only the base of the wire is exposed. The arm 140 is pivotally attached to base 12.

To accommodate upward vertical travel of the transfer membrane, as will be seen, the reservoir 78 at the end of the gel 42 at which that transfer takes place is extended downward about assembly 70 as a lower reservoir 146. Wells 136 are cast into gel 42 to load the material under analysis.

Variations in collection efficiency are minimized by constraining the motion of the collecting surface to a linear path and by stabilizing the collecting membrane in the collecting region by minimizing contact pressure and by providing a controlled tension in the plane of the membrane. Collecting surface damage and reprinting are eliminated and the bands of fragments are transferred accurately.

The membrane is provided in sheet form just large enough to hold the separated bands. The sheet is bounded by four edges, and supported on a frame with two opposed edges clamped or affixed to the frame. The frame is constrained to move in, and is translated in, a plane transverse to the plane of the gel by controlled velocity means. It is moved in a direction away from a tension generating line contact adjacent to and beyond the end of the gel at which the transfer occurs. This provides a stable collecting surface and the gel contacts the collecting face of the membrane under a controlled pressure that is below the threshold of damage and under a controlled tension.

In the preferred embodiment to minimize the effect of surface contact, the angle of wrap of the membrane on the end of the gel slab is physically maintained at or near zero thus creating minimal contact pressure. The membrane is placed under a controlled tension during transfer. The regulating means for both of these necessary constraints comprises a spring loaded, slideable block acting in the plane of the gel slab that bears against the back of the membrane. The membrane is, biased away from the membrane-holding frame and against the gel. The biasing action and the structure of the gel holder and the block provides a line contact or pinch zone across the face of the membrane adjacent to the contact of the membrane with the gel disposed in a direction away from the direction of relative motion so that the motion of the frame during transfer creates tension in the membrane to hold it smooth and properly located relative to the end of the gel. This pressure is preselected as it is a function of the spring constant of the biasing springs. Because the slideable block contacts the membrane in line with the end of the gel holder, the angle of wrap of the membrane about the end of the gel is held substantially to zero to thus maintain the contact pressure at a minimal level.

A buffer reservoir in the chamber in which the block slides holds the liquid buffer which floods the back of the membrane. An electrode is disposed in the liquid and electrical continuity is provided through the buffer and the membrane. The other (input or cathode) end of the separation gel preferably is provided with a liquid buffer reservoir preferably part of the gel holder or cassette. An electrode contacts this liquid and, preferably, is mounted on a member that permits swinging the electrode into and out of contact.

The separation and transfer apparatus described above is most amenable to automated operation. A preferred embodiment is disclosed in which separation and transfer is confined to a module disposed for this purpose and the membrane frame is moved out of this separation and transfer module vertically into a traveler which carries it to subsequent treatment modules and ultimately to a detection module all modules being under the control of computer means which also carries out identification of the separated fragments.

Figure 3:
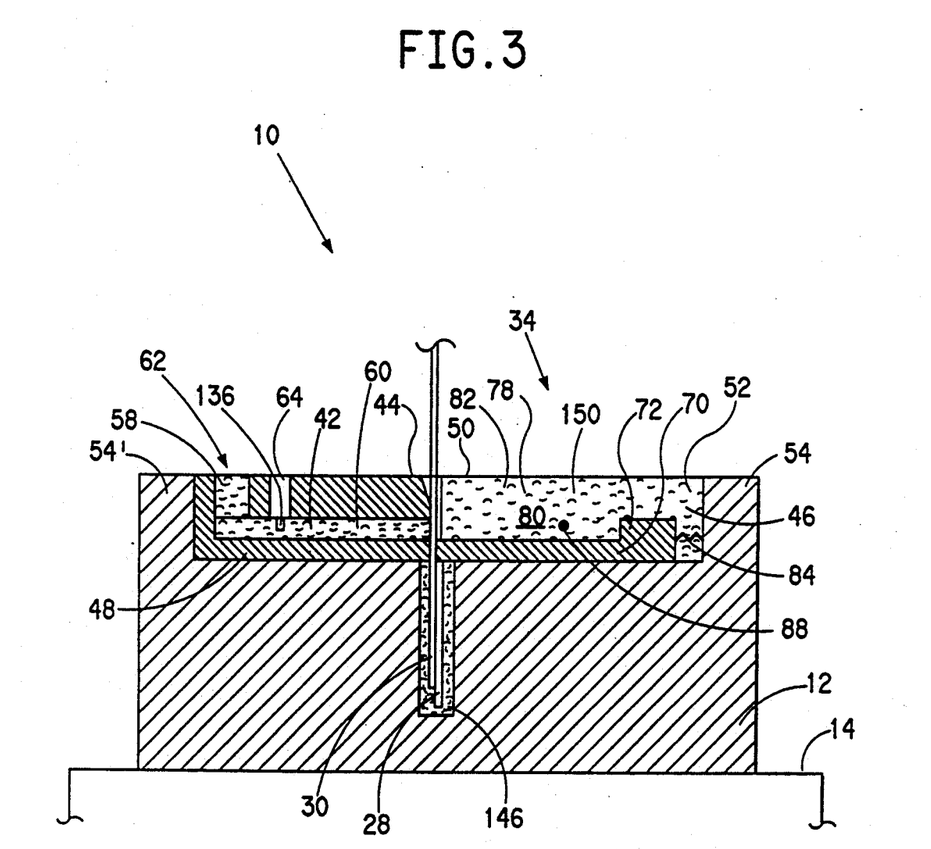
FIG. 3 is an elevational view in cross-section of that part of the apparatus that holds the gel cassette showing gel cast therein and shows a preferred fully-flooded membrane-buffer supply.

Referring now to FIG. 3, which is a cross-section of FIG. 2 taken on the line 3—3, further details of module 34 may be seen. Cavity 150 may be considered a four sided container 46 having a bottom 48, an open top 50, two sides 52, 52' and two ends 54, 54', with a lower reservoir 146 extending the full width between sides 52, 52'. In container 46, gel holder 44 is removably fitted to one side of lower reservoir 146. Note that container 46 is narrower at this end than it is at the other (see FIG. 2). Gel cassette 44 has an "L"-shaped cavity 58 with a first portion (or extended reservoir) 60 into which gel 42 is cast so that the slab formed is flush with the open end thereof and flush at the other end with the wall of a second portion 36 which forms a liquid reservoir 62 for buffer. Slot 64 is provided to hold a comb, not shown in FIGS. 2 and 3, to form wells 136 in gel 42. The slab of gel 42 in first portion 60, about 1.5 mm thick preferably, forms the separation region and is cast flush with the end of first portion 60 as will be discussed in more detail later. The gel holder 44 is securely held down by screws 66, 68 (FIG. 2).

In the wider part of container 46, there is fitted the slideable assembly 70. This assembly of parts forms reservoir 78 which, in use, is filled with membrane-buffer solution 80 which contacts the back of membrane 30 to form liquid interface 82. Electrode 88 extends through reservoir 78. One or more springs 84, suitably anchored, bias slideable assembly 70 to sandwich membrane 30 between the end of slideable block 72 and the end of gel cassette 44 so that the front side of membrane 30 is proximate to the end of the gel 42 in portion 60 and the angle of wrap is substantially zero. Frame 28 is sized so that it bridges the end of assembly 70 to expose membrane 30 to a pinching line contact.

Figure 3A:
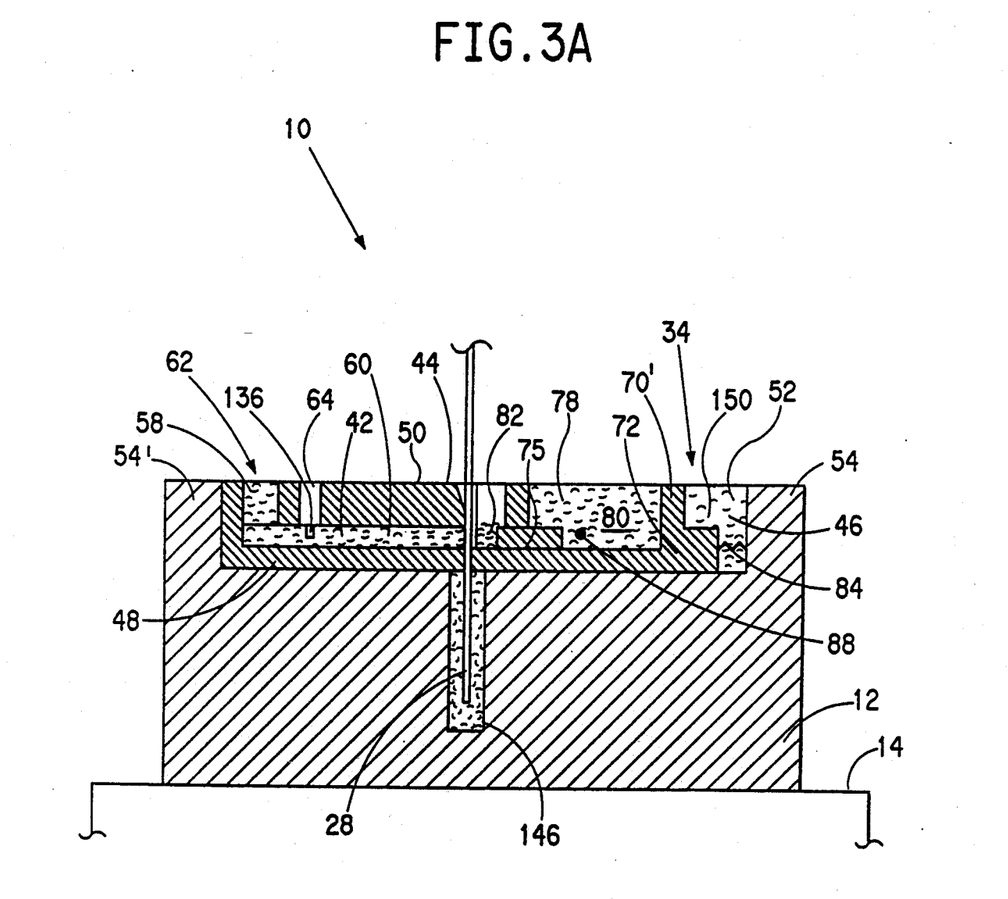
FIG. 3A is an elevational view in cross-section of the apparatus of FIG. 3 showing a slot and wick feed for membrane-buffer.

Referring now to FIG. 3A, there is seen an embodiment in which only a limited quantity of membrane-buffer is employed. This version employs much the same apparatus as reviewed earlier herein.

In the wider part of container 46, there is fitted the slideable assembly 70'. In this embodiment it is an open top unit made up of block 72' having a bottom back and two sides to which is removably fastened by means not shown a front wall 74 that holds wick 76 in slot 75 against the bottom of block 72' and extending beyond wall 74 at least in the direction of gel 42. A preferred material of construction for the wick is hydrophilic POREX TM a product of Porex Technologies. The wick, however may be made from any porous material that will not contaminate the buffer and has suitable porosity and electrical properties such as felt or paper. This assembly of parts forms reservoir 78 which, in use, is filled with buffer solution 80 which flows in a controlled manner through wick 76 to form liquid interface 82 against the back of membrane 30. Depending on the spacing of wick 76 from membrane 30, the interface may be a film or a bead. Electrode 88 extends through reservoir 78. One or more springs 84, suitably anchored, bias slideable assembly 70' to sandwich membrane 30 between the end of slideable well assembly 70' and the end of gel holder 44 so that the front side of membrane 30 is proximate to the end of the gel in portion 60 at a substantially zero angle of wrap. Frame 28 is sized so that it bridges the end of block 72' to expose membrane 30 to contact. The wick feed may be replaced by a slot feed. This will be discussed with reference to FIG. 4B below.

Figure 4:
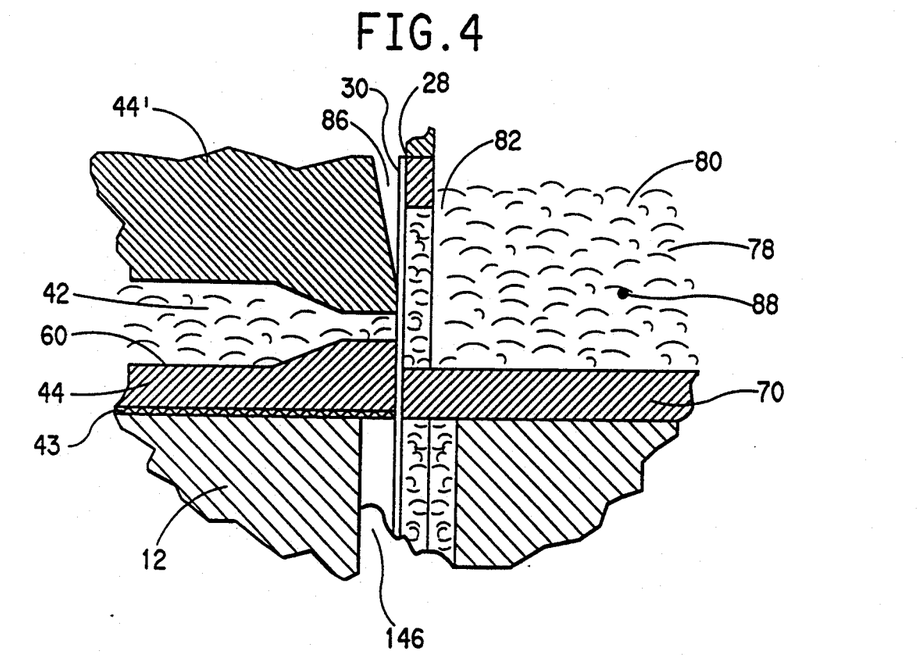
FIG. 4 is an enlarged elevational view in cross-section of the membrane-buffer feed region for the preferred apparatus of FIG. 3.

Turning now to FIG. 4 to view the transfer region in the preferred embodiment, gel 42 is cast in gel cassette 44 so that the end is flush with the end thereof. The upper part 44' of gel cassette 44 extends as far as the lower part for a small distance vertically and then is cut back leaving a gap 86 which aids in limiting surface contact on membrane 30. Note that the end of the gel 42 is constrained to a tapered shape by the configuration of portion 60. This provides electrical focusing, that is to say concentration, of the separated bands. The end of gel cassette 44 is thicker than the end of slideable assembly 70. This makes alignment in the transfer region noncritical. It also provides for a line of contact pinching the membrane 30 between the respective ends of gel cassette 44 and slideable assembly 70 to establish tension in the plane of the membrane as frame 28 is moved upwards as has been mentioned above. Membrane-buffer 80 floods reservoir 78 also as described.

Figure 4A:
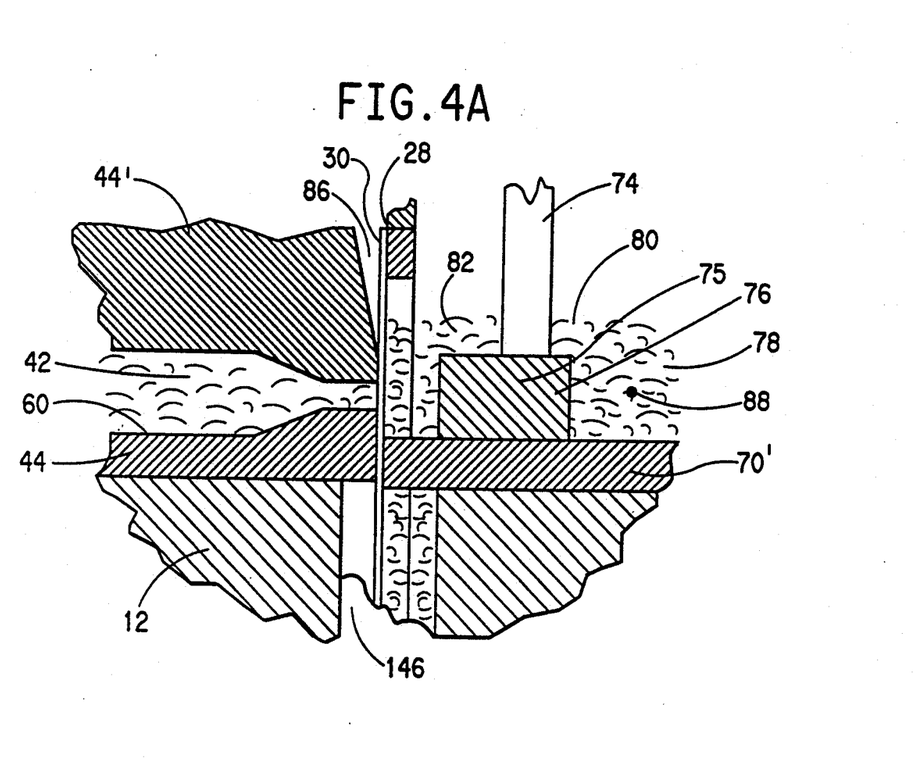
FIG. 4A is an enlarged elevational view in cross-section of the slot and associated structure employing a wick in the cassette of FIG. 3A.

Refer now to FIG. 4A to view the transfer region in the embodiment where it is desired to minimize the amount of membrane-buffer used. In general the description of the flooded assembly holds here as well. The slideable assembly 70' is converted into a slideable reservoir having a forward wall 74 under which a slot 75 is closed with a wick 76 as seen previously. Wick 76 may touch the back of membrane 30 but preferably is spaced away as shown in the figure.

Figure 4B:
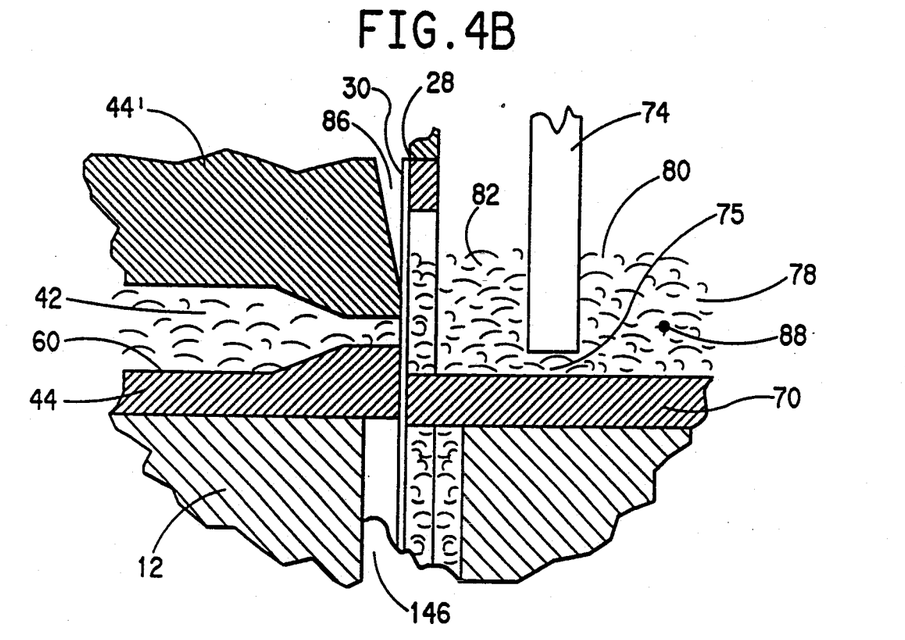
FIG. 4B is similar to FIG. 4A but shows an embodiment that employs a slot feed in place of a wick.

In FIG. 4B, a simpler construction is shown in which there is no wick 76. It has been found that submerged slot 75 suitably reduced in height meters buffer at a reasonable rate to carry out the desired electrophoresis in most instances.

Both of these latter two limited supply systems are less preferred than the flooded arrangement because with the limited supply of buffer there is also an increased probability of bubbles by starving the interface at the membrane. This produces distorted blots. If interface 82 is too small, surface tension can be a negative and smear the blots.

Figure 5:
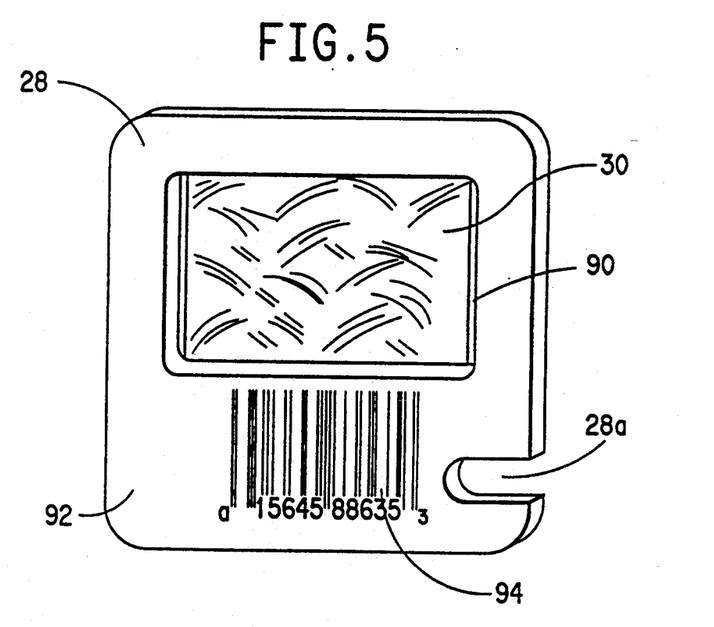
FIG. 5 is a perspective view of a frame holding a transfer membrane according to the invention.

Frame 28 as seen in FIG. 5 is a thin plate preferably fabricated from a plastic such as polystyrene with an opening 90 to accommodate membrane 30. Membrane 30, ordinarily made from nylon, is attached to frame 28 only at the top and bottom by use of an adhesive or by heat or ultrasonic sealing. This prevents any rippling when a load is applied normal to the surface. For the same reason, we may cut the membrane somewhat smaller than the opening 90 in the direction transverse to the direction of travel during transfer as seen in the figure. However there is an advantage to having the membrane overlapping all sides of the frame if it is desired to seal the periphery during subsequent processing. Thus either configuration may be used depending on the particular system chosen. Frame 28 preferably is provided with an identification region 92 where a sample identification such as bar code 94 may be placed. Also preferably, it has an orientation slot 28a to facilitate proper processing alignment and/or to signal position.

Figure 7:
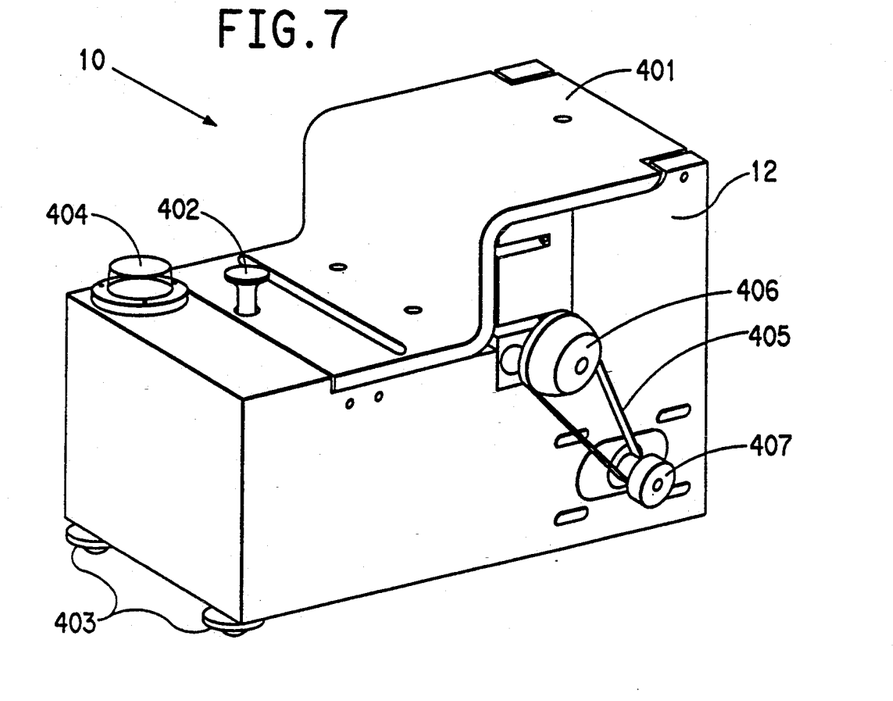
FIG. 7 is a perspective view of an embodiment of the apparatus of FIG. 1 configured for bench separation service.

FIG. 7 shows an embodiment of the transfer apparatus 10 of FIG. 1 in which the mechanism that moves a membrane frame 28 and its associated membrane 30 is internal to the base 12. The embodiment of FIG. 7 is distinguished further in being aimed at convenient, manual bench operation and not at incorporation in an automated handling system. Thus the base 12 is capped by lid 401 which is removable using handle 402. Base 12 is equipped with leveling means such as adjustable feet 403 and may have a level indicator 404. A belt 405 interconnects pulleys 406 and 407.

Figure 8:
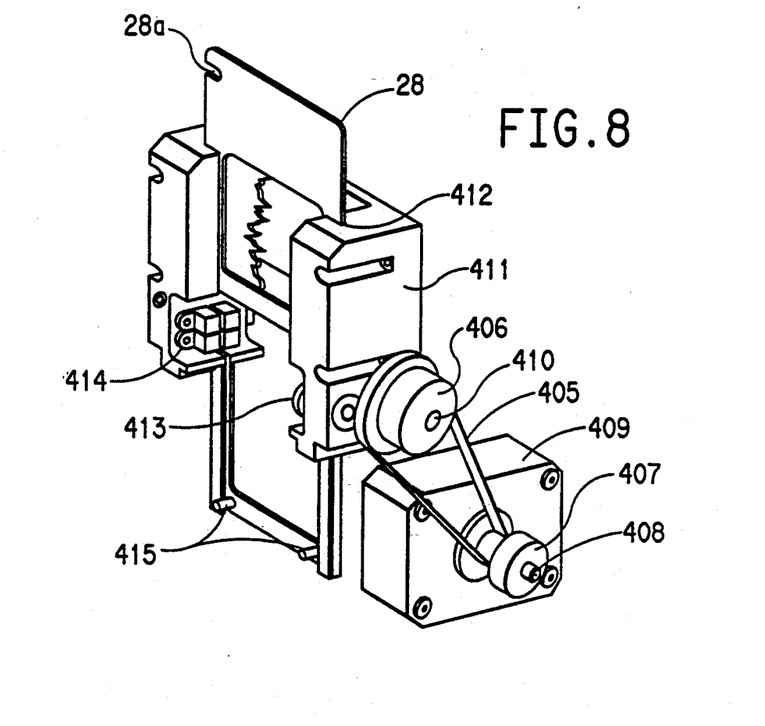
FIG. 8 is a perspective view of a vertical transport mechanism employed in the embodiment of FIG. 7.

The membrane drive mechanism is shown in more detail in FIG. 8. Pulley 407 is mounted on the shaft 408 of motor 409. Pulley 406 on shaft 410 is mounted on body 411 and has an elastomeric covered tire (not seen) on the other end. This tire contacts the face of membrane frame 28 along one edge as it rides in vertical grooves 412 in body 411. Opposing the tire is roller 413. In an alternate embodiment, roller 413 is eliminated and the tire presses frame 28 against the opposite side of groove 412 to obtain traction. To provide a suitable coefficient of friction in this instance, the outer part of body 411 and hence groove 412 is made from a low friction engineering plastic such as Delrin ™ (available from E. I. du Pont de Nemours and Company, Wilmington, Del.).

Sensor device 414, actually two associated optical sensors with integral light sources, forms part of the control system and is used to verify the entry of membrane frame 28 into the lower part of the mechanism and its presence fully engaged with stops 415 in the operative location and assure that the frame is properly oriented. This is done by locating notch 28a so that it is placed at the lower sensor where it does not interrupt a beam when the bottom of the frame 28 is fully engaged with the stops while at the same time the upper corner of frame 28 interrupts the beam of the upper sensor.

In use, base 12 (of FIG. 1) is placed on platform 14 (the platform may be eliminated by incorporating leveling features into base 12 itself as seen in FIG. 7 at 403). Gel cassette 44 usually with gel 42 cast in place (with the dams needed for gel casting as is known and the comb or well former mentioned above removed) is fastened in place in container 46. Membrane 30 in frame 28 is held in deep well 146 connected to carrier 26 as described previously, and slideable well assembly 70 is installed in the larger end of container 46. Arm 140 is swung over so that electrode 38 contacts the buffer solution 80 placed on top of gel 42 in portion 62 and buffer solution 80 is placed in reservoir 78. The apparatus of FIG. 7 has the electrode (not shown) attached to the underside of the lid 401. Thus the operator simply closes the lid to bring the electrode into place.

Wells 136 are loaded with analysate and electrophoresis is carried out as is known by impressing a suitable voltage drop across electrodes 38 and 88 so that the ions migrate toward the membrane end and, when sufficient time has elapsed, motor 18 is actuated to drive membrane 30 upwardly to collect and bind the separated material in bands as is known.

Membrane frame 28 may then be removed from membrane carrier 26 either manually or automatically and forwarded for further processing of the membrane 30 and the bands of separated material thereon.

The preceding description is in the context of a horizontally arrayed gel slab with a membrane movable vertically. The critical features of the method and apparatus, however, may well be applied to a vertical gel in an apparatus in which the membrane is movable horizontally at least in the transfer region. Moreover other orientations of membrane and gel are possible as is readily apparent to one skilled in the art. For example, the membrane may move at 45 degrees relative to the gel as it rises out of the buffer solution. Thus while the description herein is directed to substantially orthogonal contact and disposition of membrane and gel, other arrangements are contemplated herein as may be suitable to the researcher.

Figure 6:
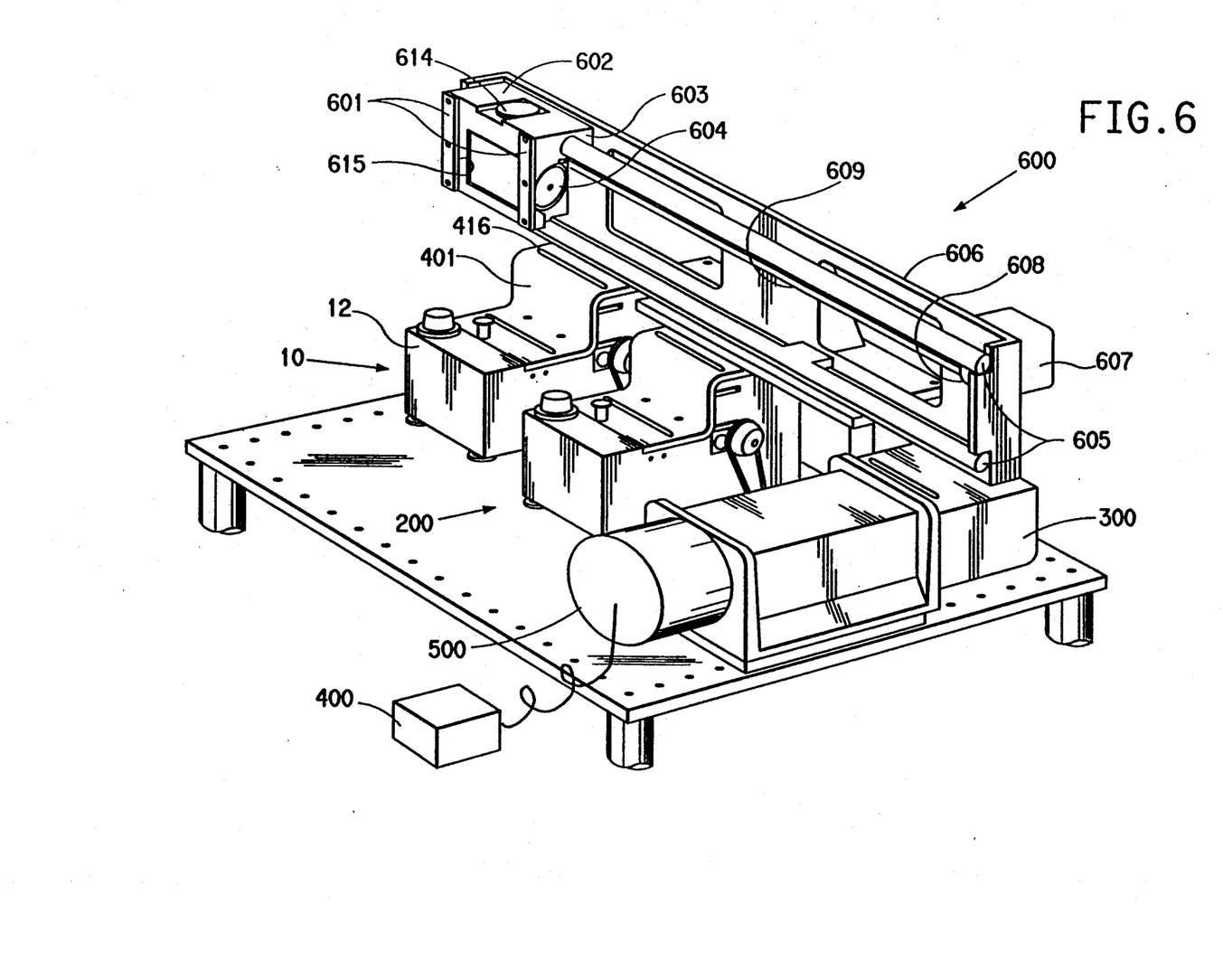
FIG. 6 is a schematic perspective view of a preferred embodiment of the invention which incorporates automated processing of the transfer membrane to provide identification of the separated species.

FIG. 6 shows a preferred form of apparatus 10 incorporated into apparatus, generally designated 600, for automated processing in a system for identification of organisms or the like.

Details of base 12 are not shown. They are generally as seen in FIG. 8. Vertical transport to move frame 28 upwardly to collect the separated species uses the apparatus described before. A frame 28 initially is inserted manually to engagement with stops 415 which puts the frame 28 in the operating position shown in FIG. 3. When electrophoresis is started, motor 409 is energized and drives the frame upwardly at a controlled rate to collect the separated bands of DNA.

When electrophoresis is complete, frame 28 is driven upwardly through slot 416 in cover 401 and into the grooves 615 formed between strips 601 and the body 602 of traveler 603. It is pinched against one of strips 601 by tire 604 which is controlled by a motor not seen. Traveler 603 translates on guide rails 605 in suitable linear bearings not shown. The rails are attached to structure 606. Sensor 614 located atop traveler 603 acts in two ways. When a frame 28 is delivered into the top of the grooves 615 and driven downwardly, the sensor 615 senses the presence of frame 28 and the absence of the top edge causes the control system to stop the drive. This locates the top of frame 28 flush with the sensor. When a frame 28 is delivered to the bottom of grooves 615 and the drive acts upwardly, sensor 614 senses the absence of the frame 28 and the presence of the top edge stops the drive again obtaining proper location.

Traveler 603 is translated by motor 607 which drives one of a pair of pulleys 608 (only one of which is visible in the figure) acting on belt 609 (preferably a timing belt) which is fastened to traveler 603.

In line with separation and transfer apparatus 10 is at least one processing module 200 which is similarly supplied with vertical transport apparatus as described above for separation module 10 but otherwise differs in its internals. Such a module may be equipped solely to immobilize and denature DNA fragments using a suitable reagent and including drying means if required. Then, in a subsequent module, hybridization could be accomplished and needed washes could be done in still further modules followed by blocking, incubation and labeling with a chemiluminescent marker. Frame 28 would be moved from module to module as required. The procedure in which a frame 28 is handed off between the sets of vertical transports, one in the fixed module and the other in the traveler 603, facilitates this processing procedure by raising the bottom of the frame high enough to clear any intervening module or part thereof. Thus this feature supports random processing with any number of intermediate stations. A module 200 may also be fitted to perform all of the above or different processing steps in the single module.

When membrane 30 is fully treated it is transported to detection module 300 where it is positioned for reading by detection device 500 which we prefer to be a CCD camera. Data from detection device 500 is fed to process control means 400, preferably a minicomputer, where analysis of the band pattern is done by methods known in the art.

Upon completion of the reading or scanning of the information on the membrane 30, it, along with the frame 28 which carries it, is discharged or "dumped" to a sanitary waste, not shown, for proper disposal. We prefer to discharge the spent item through a slot (not shown) in the bottom of module 300 and table 14 using gravity and an escapement to control both the dumping and necessary light shielding and locating.

Figure 9:
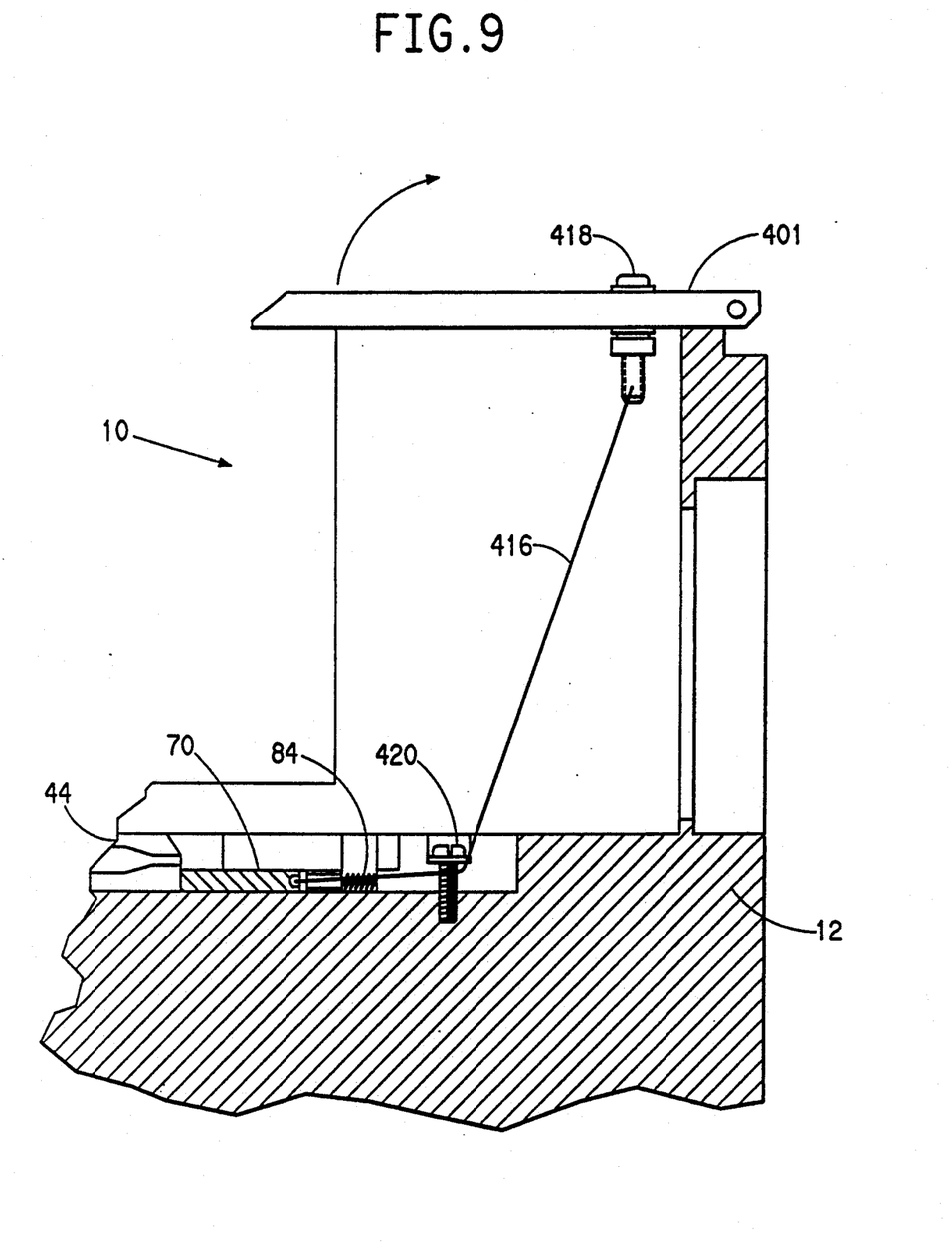
FIG. 9 is a cross-sectional elevational view of a pressure relief mechanism used in loading the invention with a transfer membrane.

The processing cycle is, of course, repeated after dumping. It is clear that a frame 28 could hang up on the top edge of assembly 70 if the assembly was not retracted during the loading operation. Referring now to FIG. 9, there is seen a cross-section of a portion of apparatus 10 showing a means for such retraction in a module intended for stand-alone, semi-automatic operation in the configuration of FIG. 7. When lid 401 is raised, ligature 416 is tensioned as it is attached at one end to fastener 418 affixed to lid 401. Ligature 416 is a nylon monofilament or the like. The ligature passes around turning bar 420 which is mounted to base 12 and is attached to slideable assembly 70 (which acts as a pressure bar to tension the membranes). Tensioning ligature 416 pulls slideable assembly 70 back from contact with cassette 44 compressing springs 84. The reverse action occurs when the lid is closed. For automatic operation, there being no pivoted lid involved, the ligature is tensioned by a solenoid or the like at a suitable programmed time or, more preferably, when used in conjunction with traveler 603 can be cammed in and out of position by a lever actuated by the presence of the traveler.

It also will be plain to those of skill in this art that module 300 might well be equipped with the same vertical transport mechanism used in the modules 10 and 200 which would permit transporting a spent frame/membrane 28/30 upwards into traveler 603 which then could be directed to move on an extended structure 606 (and associated components) outboard of table 14 where the dumping would occur.

Orderly, properly-timed, processing is under the control of control means 400 which actuates the various stepping motors to carry out the needed functions. To provide time balancing, modules may be duplicated so that more than one membrane frame 28 is processed simultaneously. Similarly, where wash steps are provided in a dedicated module or modules, a membrane frame 28 may be returned toward the starting end of the transport system to such a module.

Where a protocol may require temperature control for the gel 42, optionally we provide a temperature control means 43 (shown on FIG. 4) with an associated temperature sensing means and controller (not shown). This is located beneath gel cassette 44. For heating we employ a Minco sealed immersible heater (model HK5418R51.8L12B-9102) and an RTD as a sensor.

We have found that the unbonded leading edge of membrane 30 can damage the edge of gel 42 if it is allowed to pass across the face of gel 42 during loading. The leading edge is that portion of the membrane 30 which first passes proximate to the gel 42, upon entry or discharge of a membrane/frame assembly 30/28. The portion of the edge peripherally exterior to the bond seam is the unbonded leading edge. This edge has a tendency to chip or scar the gel during loading and unloading operations. Accordingly, in the embodiments described previously, we have provided devices to unload the contact pressure during loading as described above (for example see FIG. 9).

We have also found that a well made frame/membrane assembly 28/30 has the frame bowed ever so slightly away from the membrane because of the tension in the membrane 30. (This bow is exaggerated in FIG. 10 for purposes of illustration). This is particularly true with regard to our preferred ultrasonically bonded units.

In fabrication we ultrasonically bond one edge of the membrane to the frame. Then we deliberately bow the frame away from the membrane so that the concave side so formed faces the membrane. We next ultrasonically bond the opposite edge of the membrane to the frame, while the membrane is under some applied tension. The requisite tension is sufficient to hold the membrane straight and flat. This can be accomplished as by the experimenter pulling the free end of the membrane, or by other means.

Another way to make the tensioned frame is as follows:

A frame is laid on a vacuum fixture that has a vacuum pad beneath the anvil of an ultrasonic bonder and a pad under the window area of the frame. A membrane is placed in position; both pads are turned on. The bonder is turned on and one end of the membrane fixed to the frame. The vacuum is turned off and the frame reversed in the fixture. Vacuum is turned on under the anvil only and the frame is manually clamped at both sides near the mid portion. The frame is manually pulled toward the operator, sliding under the clamps, and the edge the operator is pulling is elevated on a fixture that bends the frame away from the taut membrane. The bonder is turned on and the second end of the membrane is fixed to the frame. The vacuum is turned off and the clamps released permitting the frame to spring back to a very slightly bowed shape.

We use this bowing to advantage in still another embodiment as will be seen.

Figure 10:
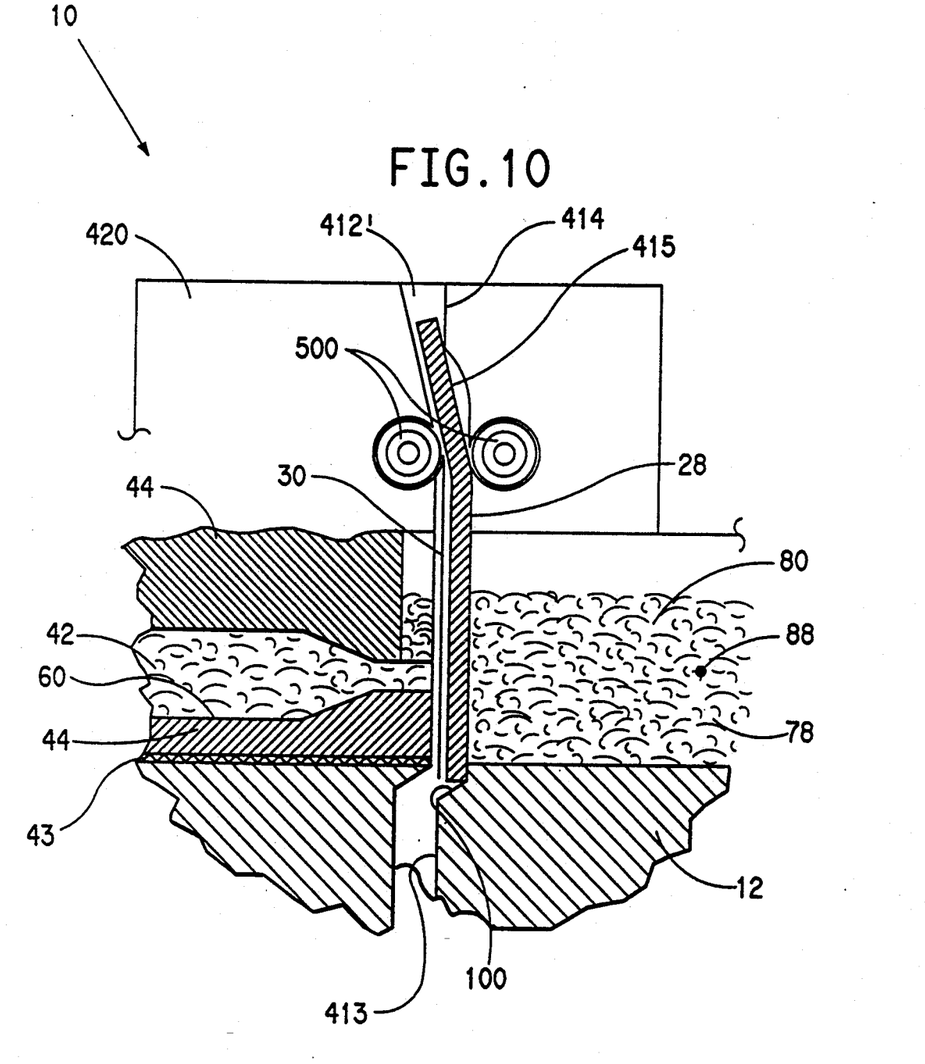
FIG. 10 is a partial cross-sectional elevational view of a preferred simplified embodiment with loading means.

In FIG. 10 there is shown a simplified embodiment which eliminates the sliding block and the associated spring biasing means and avoids scarring of the gel during loading even though there is no direct pressure relief mechanism involved. Frame 28 is initially constrained to slide at an angle to vertical. We prefer an angle of about 10 degrees. The portion 414 is vertical and spaced about 0.045 inches from the vertical wall pf part 415 or something less than the thickness of a frame. Moving the portion 414 to a greater distance would cause unnecessary frame bending. While the preferred angle of the initial part of the guiding groove is about 10 degrees, the important principle is to clear the end of the gel and to contact the far wall at an angle that will not lock. Frame 28 and its attached membrane 30 moves downward during loading, driven by rubber-tired rollers 500 acting on the outside edges of frame 28, in groove 412', and is constrained by walls 100.

We prefer roller pairs at both sides and to drive all of the rollers. Rolls 500 are covered with 70 durometer rubber and are placed to provide about 12 mils squeeze on the frame 28. The angled approach allows the unbonded leading edge of membrane to clear the end of gel 42 as the frame 28 strikes the far wall 100 which cams the lower end of frame 28 toward gel 42. With continued motion, the frame conforms to the vertical portion 413 of groove 412' as it enters. We space this wall the thickness of the frame 28 away from the end of gel 42 (and carrier 44). In our preferred embodiments, the frame thickness is 0.060 inches and so we allow 0.003 inches clearance for a spacing of 0.063 inches plus or minus 0.001 inches. Of course, these dimensions are dependent on the dimensions of the overall assembly and may vary according to the size requirements desired. Continued motion bends the frame to conform to the vertical portion 413 of groove 412' as it enters. Groove 412' is formed in structure 420 which is provided at opposite sides of the unit 10. The top of frame 28 then clears the end of the angled portion 414 and snaps to the far side of the widened part 415 to take up a vertical position as it is driven downward to the starting position. There the groove location, the roller contact, and the slight bowing of the frame away from the membrane mentioned above cause the membrane 30 to slide under tension past the end of gel carrier 44 creating the desired line of tension ahead of contact with the end of gel 42 when the frame 28 is driven upward. Continued upward motion of the frame 28 towards widened portion 415 cams the top back into the angled portion 414 for discharge.

This configuration permits considerable size reduction and reduces the number of parts.

What is claimed is:

1. Apparatus for gel electrophoresis in which molecular fragments in a solution are separated electrophoretically across a gel, comprising:
   (a) an electrophoresis module comprising the gel including the solution with molecular fragments and means for effecting electrophoresis therealong;
   (b) an electrophoretic transfer membrane comprising a frame that supports a flexible membrane along portions of the periphery thereof;
   (c) means for moving said electrophoretic transfer membrane relative to and in proximity to said electrophoresis module, so that the molecular fragments are received on said flexible membrane from said gel; and
   (d) means for tensioning said flexible membrane as said electrophoretic transfer membrane moves in proximity to said electrophoresis module.

2. The apparatus of claim 1 wherein in said electrophoresis module (a) said means for effecting electrophoresis comprises (i) a cassette having a first reservoir adapted to receive buffer solution and a first electrode and an extended portion adapted to receive the gel, said first reservoir positioned at a first location relative to said extended portion, and (ii) a second reservoir having buffer solution and a second electrode and positioned at a second location relative to said extended portion, and further wherein the gel including solution with molecular fragments is positioned within said extended portion and between said first and second reservoirs, and further wherein a voltage differential is applied between said first and second electrodes to electrophoretically translate and separate the molecular fragments toward one end of said gel proximate to said electrophoretic transfer membrane (b).

3. The apparatus of claim 2 wherein in said electrophoresis module (a) said cassette is configured in an "L"-shaped pattern wherein said first reservoir and said extended portion are positioned substantially perpendicularly to one another, and wherein said extended portion extends lengthwise horizontally and said first reservoir extends lengthwise vertically.

4. The apparatus of claim 2 wherein said extended portion has a rectangular cross section of a width at least 10 times greater than the height suitable for casting therein of a planar gel slab.

5. The apparatus of claim 2 wherein said extended portion includes an upper surface having an aperture therein suitable for casting integral wells within the gel, said wells adapted to contain the solution including molecular fragments for electrophoresis.

6. The apparatus of claim 2 wherein said extended portion has a distal end, and at least said distal end is configured as having progressively decreasing height, from the first reservoir and extending therealong.

7. The apparatus of claim 2 wherein said first electrode is mounted on a swingably openable portion attached to the electrophoresis module.

8. The apparatus of claim 2 wherein the buffer in said second reservoir (ii) is in fluid contact with the flexible membrane of the electrophoretic transfer membrane (b) via a slot formed in one end of said reservoir (ii) which is proximate to said transfer membrane (b).

9. The apparatus of claim 8 wherein said slot contains a wick therein to meter flow of buffer from said reservoir (ii) to said transfer membrane (b).

10. The apparatus of claim 1 wherein said means (c) for moving said electrophoretic transfer membrane comprises a rotatable member contacting said frame and which is operably connected to a motor and drive train assembly, sufficient to move said electrophoretic transfer membrane relative to and proximate to said electrophoresis module (a).

11. The apparatus of claim 2 wherein said means (d) for tensioning the flexible membrane comprises a means for generating line contact at a desired tension on said flexible membrane adjacent to the end of said gel proximate to said electrophoretic transfer membrane (b).

12. The apparatus of claim 11 wherein said means for generating line contact comprises a displaceable member and biasing means positioned within said second reservoir (ii) and wherein said displaceable member contacts and displaces said flexible membrane toward said gel.

13. The apparatus of claim 2 wherein in said electrophoretic transfer membrane (b) said frame is bowed away from said flexible membrane, and said flexible membrane has one or more unbonded edges; and further wherein said means (c) for moving said electrophoretic transfer membrane further comprises at least two rollers positioned to drive said frame through a slot disposed at sufficient degrees from vertical so that the unbonded edges do not contact said gel, and means for camming said frame to vertical position so that the molecular fragments are received on said flexible membrane from said gel; and further wherein said means (d) for tensioning said flexible membrane comprises the combination of said rollers, said frame which is bowed and in vertical position, and said second reservoir.

14. The apparatus of claim 13 wherein said slot is disposed at about 10 degrees from vertical.

15. Apparatus for automated gel electrophoresis of molecular components, direct blot transfer of the components to an electrophoretic transfer membrane, processing of the membrane and detection of the components thereon, comprising:
(1) a separation and direct blot transfer module comprising
  (a) an electrophoresis module comprising the gel including the solution with molecular fragments and means for effecting electrophoresis therealong;
  (b) an electrophoretic transfer membrane comprising a frame that supports a flexible membrane along portions of the periphery thereof;
  (c) means for moving said electrophoretic transfer membrane relative to and in proximity to said electrophoresis module, so that the molecular fragments are received on said flexible membrane from said gel; and
  (d) means for tensioning said flexible membrane as said electrophoretic transfer membrane moves in proximity to said electrophoresis module;
(2) one or more membrane processing modules positioned in alignment with said separation and direct blot transfer module (1);
(3) a detection module positioned in alignment with said separation and direct blot transfer module (1) and said membrane processing modules (2);
(4) linear transport means operable to move said electrophoretic transfer membrane among said modules (1), (2), and (3); and
(5) control means operable to integrate and control the functioning of said modules (1), (2), and (3) in concert with said linear transport means.

16. A process for gel electrophoresis of molecular fragments, comprising:
(a) introducing a gel including a solution with the molecular fragments therein, into an electrophoresis module having means for effecting electrophoresis therealong;
(b) positioning an electrophoretic transfer membrane for contact with said gel, said electrophoretic transfer membrane comprising a frame that supports a flexible membrane along portions of the periphery thereof;
(c) moving said electrophoretic transfer membrane relative to and in proximity to said electrophoresis module, so that the molecular fragments are received on said flexible membrane from said gel; and
(d) tensioning said flexible membrane as said electrophoretic transfer membrane moves in proximity to said electrophoresis module.

* * * * *